United States Patent [19]

Lin

[11] 4,139,516
[45] Feb. 13, 1979

[54] PROCESS FOR THE PREPARATION OF THIANTHRENE COMPOUNDS

[75] Inventor: Henry C. Lin, Grand Island, N.Y.

[73] Assignee: Hooker Chemicals & Plastics Corp., Niagara Falls, N.Y.

[21] Appl. No.: 822,181

[22] Filed: Aug. 5, 1977

[51] Int. Cl.$^2$ ........................................... C07D 339/08
[52] U.S. Cl. ................................................ 260/327 P
[58] Field of Search ..................................... 260/327 P

[56] References Cited

U.S. PATENT DOCUMENTS

| 3,997,560 | 12/1976 | Buckholtz et al. | 260/327 P |
| 4,091,031 | 5/1978 | Buckholtz et al. | 260/327 P |

OTHER PUBLICATIONS

Fieser et al., Adv. Org. Chem. (Reinhold, 1962), p. 19.
Morrison et al., Org. Chem. (Allyn & Bacon, 1974), pp. 32–35.
Gilman et al, J. Am. Chem. Soc. vol. 78, pp. 2163 to 2165 (1956).

Primary Examiner—John D. Randolph
Attorney, Agent, or Firm—Peter F. Casella; William J. Crossetta, Jr.; Arthur S. Cookfair

[57] ABSTRACT

A process for the preparation of a thianthrene compound which comprises

A. adding sulfur monochloride to an excess of a selected benzene compound in the presence of aluminum chloride and reacting to form a thianthrene compound: aluminum chloride complex in the reaction medium;

B. treating the reaction medium with an alcohol to free the thianthrene compound from the complex and dissolve the aluminum chloride therein;

C. separating the thianthrene compound from the reaction medium;

Preferred benzene compounds include benzene and substituted benzene compounds, especially halobenzenes, alkylbenzenes, and the like having at least two adjacent ring positions unsubstituted.

6 Claims, No Drawings

PROCESS FOR THE PREPARATION OF THIANTHRENE COMPOUNDS

BACKGROUND OF THE INVENTION

This invention relates to an improved process for the manufacture of thianthrene compounds. Thianthrene and substituted compounds are useful in a variety of chemical processes, for example, as chemical intermediates in the preparation of dyestuffs such as thianthrene vat dyes. In addition, various thianthrene compounds are useful plasticizers, pesticides, and flameproofing agents. Recently it has been found that thianthrene compounds having electron withdrawing substitutents such as halogens, on the aromatic nuclei thereof are especially useful as components of catalyst systems for the directed nuclear chlorination of alkylbenzenes. Although thianthrene compounds have been known for many years, little effort has been directed toward the development of a process suitable for commercial manufacture.

One method described in the prior art (J.A.C.S., Vol. 78, 2163-2164, 1956) comprises reacting sulfur monochloride with refluxing benzene in the presence of aluminum chloride. The reaction product is then treated with iced hydrochloric acid and steam distilled to remove benzene and steam volatile impurities. The aqueous layer is then decanted off, and the residue filtered. The product is warmed with a sodium hydroxide solution, filtered and washed successively with water and ethanol. The residue is refluxed with an excess of glacial acetic acid, cooled, filtered and washed with ethanol to give 86% yield of crude brown thianthrene. The purity of the product may be improved (with a consequent decrease in yield) by additional distillation and recrystallization from glacial acetic acid.

While this laboratory scale method produces thianthrene, many disadvantages prevent its adoption for large scale commercial production. The method involves numerous unit operations to make pure thianthrene (no data is indicated in the literature on the percent purity of thianthrene attainable). Additional drawbacks to the adaptation of such a method to commercial production include the use of substantial quantities of extremely corrosive glacial acetic acid. Furthermore the thianthrene produced remains contaminated and occluded with by-product sulfur and diphenyl sulfide.

In a more recent development, it has been disclosed (U.S. Pat. No. 3,997,560, Dec. 14, 1976; and U.S. Pat. application Ser. No. 137,320, filed Nov. 1, 1976) that thianthrene compounds may be prepared by adding sulfur monochloride to an excess of a benzene compound in the presence of aluminum chloride, and reacting to form a thianthrene compound as an insoluble aluminum chloride complex; slurrying the complex in an inert inorganic liquid; treating the slurry with a Lewis base, such as ammonia pyridine, dimethylamine or the like, to free the thianthrene compound from the complex, and dissolving the thianthrene in an organic solvent therefor. Although the process disclosed is useful for the preparation of thianthrene compounds and adaptable to commercial production thereof, large scale operation presents certain difficulties, including for example, the use of large amounts of ammonia, and the noxious vapors thereof, and the need to further recover the desired thianthrene compound from solution in the organic solvent.

It is an object of the present invention to provide a process for the production and recovery of thianthrene based products which is direct and simple and which is adaptable to large scale commercial operations. A further object is to provide an improved method whereby a solid high purity thianthrene product may be produced in high yields. A still further object is to provide an improved process for the recovery of thianthrene compounds from a thianthrene compound-aluminum chloride complex.

SUMMARY OF THE INVENTION

It has now been found that thianthrene compounds may be prepared by a process comprising:

A. adding sulfur monochloride to an excess of a benzene compound in the presence of aluminum chloride and reacting to form a thianthrene compound: aluminum chloride complex in the reaction medium;

B. treating the reaction medium with an alcohol to free the thianthrene compound from the complex and dissolve the aluminum chloride therein;

C. separating the thianthrene compound from the reaction medium.

In the process, it is preferred that sulfur monochloride be added to the benzene compound rather than the reverse, since the addition of the benzene compound to sulfur monochloride may result in the formation of undesirable polymeric sulfur products. Furthermore, the addition of the sulfur monochloride is made slowly to prevent excessively brisk evolution of hydrogen chloride gas. To maintain a reaction medium of suitable consistency for agitation and flow through pipelines, it is preferred, though not essential, to employ a molar ratio of benzene compound: sulfur monochloride of about 5.0:1 or greater. Based on optimization of subsequent alcohol treatment it is preferred to provide a molar ratio of benzene compound: sulfur monochloride in the range of about 5.0:1 to about 12.0:1. It will be appreciated, however, that higher or lower ratios may be employed if desired.

The amount of aluminum chloride present may vary considerably. However, we have found that maximum yields of thianthrene compound and minimum production of by-product substituted diphenyl sulfides and the like are achieved when aluminum chloride is employed in a mole ratio of aluminum chloride: sulfur monochloride of between about 0.1:1 and 1.6:1. At lower ratios the yield of thianthrene compound is lowered. At higher ratios, the yield of thianthrene compound is lowered and the production of diphenyl sulfides increased. The temperature of the reaction may vary considerably, for example, from about 20° Celsius or below to the boiling point of the benzene compound. Preferably, the reaction temperature is maintained at about 30° to about 160° Celsius. The process is preferably carried out at atmospheric pressure, although subatmospheric and superatmospheric conditions may be employed, if desired, with appropriate adjustments in the upper temperature limit.

Upon completion of the reaction, the reaction medium, comprising a mixture of insoluble thianthrene compound: aluminum chloride complex and by-product sulfur or sulfide compounds in benzene compound, is cooled to about room temperature or lower, e.g. 20°–25° Celsius and maintained thereat while alcohol, is added slowly. The alcohol addition serves a three-fold purpose: (1) to decompose the thianthrene: aluminum chloride complex and dissolve aluminum chloride (2) to dissolve the by-product sulfides and other impurities and (3) to solidify the thianthrene compound product. The amount of alcohol added may vary considerably and may be in amounts as low as a weight ratio of 0.5:1 or less of alcohol: excess benzene compound. At very low ratios, however, the dissolution of aluminum chloride in alcohol may be incomplete and some of the thianthrene may dissolve in the excess benzene compound. To obtain optimum yields and purity of product the alcohol is preferably employed in an amount sufficient to substantially dissolve the aluminum chloride and prevent the dissolving of thianthrene in the excess benzene compound. The weight ratio of alcohol: excess benzene compound may be as much as 8:1 or higher. However, from an economic point of view the use of excessively high amounts of alcohol may be unnecessarily wasteful and in addition will dissolve small amounts of thianthrene. For this reason it is preferred to employ a weight ratio of alcohol: excess benzene compound of less than about 5:1. Following the addition of the alcohol, the solid thianthrene compound may be separated from the reaction mixture, for example, by simple filtration and, if desired the solid product may be further washed with additional alcohol and air-dried. The alcohol may be recovered in a known manner, such as by distillation and recycled, if desired.

Alcohols which may be employed in the process of this invention include, for example, aliphatic alcohols, including substituted aliphatic alcohols wherein the substituents are non-reactive under process conditions, which are liquid at the temperature employed. Preferred are branched or straight-chain aliphatic alcohols of one to ten carbon atoms, and most preferably one to four carbon atoms, especially methanol, n-butanol, isobutanol, and the like.

The thianthrenes which may be prepared in accordance with this invention are those characterized by the formula

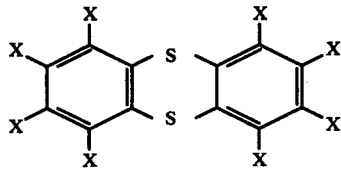

wherein each X is independently selected from the group consisting of hydrogen, methyl, ethyl, chlorine, bromine and fluorine. Most preferred are the di- and tetra-substituted thianthrenes wherein the substituents are selected from methyl and chlorine. Such compounds are prepared in the manner described from an appropriately selected benzene compound having at least two adjacent ring positions unsubstituted. The benzene compound starting materials are characterized by the formula

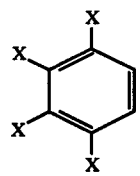

wherein each X is independently selected from the group consisting of hydrogen, methyl, ethyl, chlorine, bromine and fluorine. Most preferred are mono- and di-substituted benzene compounds wherein the substituents are independently selected from methyl and chloride. Thus, the preferred substituted benzene compound starting materials include for example, toluene, orthochlorotoluene, parachlorotoluene, metachlorotoluene, paraxylene, orthoxylene, metaxylene. The particular thianthrene compound prepared will depend on the position of the substituents on the benzene ring, and in some instances may be a mixture of thianthrene compounds. Thus, for example, when paraxylene is employed as the starting material, the thianthrene compound product will be 1,4,6,9-tetramethylthianthrene. When the starting material is metaxylene, the product will be a mixture of the 1,3,6,8- and 1,3,7,9-isomers of tetramethylthianthrene. The preferred starting material for the process of this invention, is orthochlorotoluene, the reaction product of which is a mixture of methylchlorothianthrenes comprising predominantly the 2,7 dimethyl-3,8-dichloro, and 2,8-dimethyl-3,7-dichloro-isomers, of dimethyldichlorothianthrene.

The following examples will serve to further illustrate the invention and the manner in which it may be practiced. The examples are set forth for purposes of illustration and are not to be construed as limitative of the present invention. In the examples, unless otherwise stated, all parts and percentages are by weight and all temperatures are in degrees Celsius.

EXAMPLE 1

Fifty parts of $AlCl_3$, was charged to a reaction vessel together with 562 parts of orthochlorotoluene. The mixture was heated to 50° C. and maintained thereat with stirring while 60 parts of $S_2Cl_2$ was added slowly. Following the addition of $S_2Cl_2$ the reaction mixture was maintained at 50° C. with stirring for an additional 3 hours, then cooled to room temperature (about 20° to 25° C.) and 2000 parts of methanol was added slowly, with continued stirring. During the addition of the methanol, the color of reaction mixture changed from a black to a light tan color, and the product, dimethylthianthrene began to precipitate. Following the addition of methanol the reaction mixture was filtered and the solid collected was washed with an additional 200 parts of methanol and vacuum dried. The yield was 46 parts of predominantly dimethyldichlorothianthrene as a mixture of 2,7-dimethyl-3,8-dichloro- and 2,8-dimethyl-3,7-dichloro-isomers (66 percent yield, based on $S_2Cl_2$). The solid, thus collected was analyzed by gas chromotographic techniques and found to be about 93.41 percent dimethyldichlorothianthrene, 5.47 percent dimethylmonochlorothianthrene, and 0.74 1 percent bis-(chloromethylphenyl) sulfide.

It will be appreciated by those skilled in the art, that thianthrene compounds are produced in high yield and high purity in a process substantially simpler than those known in the prior art.

EXAMPLE 2

The procedure of Example 1 was repeated except that the amount of orthochlorotoluene employed was 281 parts and the amount of methanol employed was 1000 parts. The yield was 56 parts of predominently dimethyldichlorothianthrene as a mixture of 2,7-dimethyl-3,8-dichloro- and 2,8-dimethyl-3,7-dichloro-isomers (81 percent yield based on $S_2Cl_2$). The solid product was analyzed by gas chromatography and found to be about 77.31 percent dimethyldichlorothianthrene; 17.70 percent dimethylmonochlorothianthrene; 0.96 percent dimethylthianthrene; and 1.65 percent bis-(chloromethylphenyl) sulfide.

EXAMPLE 3

The procedure of Example 1 is repeated except that in place of methanol there is employed a similar quantity of ethanol yielding a similarly high purity, dimethyldichlorothianthrene product.

EXAMPLE 4

The procedure of Example 1 is repeated except that parachlorotoluene is substituted for orthochlorotoluene. The product for thus prepared is a mixture of 1,6-dimethyl-4,9-dichlorothianthrene and 1,9-dimethyl-4,6-dichlorothianthrene.

I claim:

1. A process for the preparation of a thianthrene compound which comprises the sequential steps of
    A. adding sulfur monochloride to an excess of a benzene compound in the presence of aluminum chloride in a molar ratio of benzene compound to sulfur monochloride of about 5:1 to about 12:1 and a molar ratio of aluminum chloride:sulfur monochloride about 0.1:1 to about 1.6:1 and reacting at a temperature of between about 20° Celsius and the boiling point of the reaction mixture to form a thianthrene compound:aluminum chloride complex in the reaction medium;
    B. treating the reaction medium with an aliphatic alcohol of one to ten carbon atoms in a weight ratio of alcohol:excess benzene compound of about 0.5:1 to about 8.0:1 to free the thianthrene compound from the complex and dissolve the aluminum chloride therein;
    C. separating the thianthrene compound as a solid from the reaction medium.
2. A process according to claim 1 wherein the alcohol is an aliphatic alcohol of one to four carbon atoms.
3. A process according to claim 1 wherein the benzene compound is chlorotoluene and the thianthrene compound is dimethyldichlorothianthrene.
4. A process according to claim 1 wherein the alcohol is methanol.
5. A process according to claim 4 wherein the benzene compound is orthochlorotoluene and the thianthrene compound is dimethyldichlorothianthrene.
6. A process according to claim 1 which comprises
    A. adding $S_2Cl_2$ to orthochlorotoluene in the presence of $AlCl_3$ and reacting at a temperature of about 30° to about 160° Celsius to form a complex of aluminum chloride and dimethyldichlorothianthrene in the reaction medium;
    B. treating the reaction medium with methanol to separate the aluminum chloride from the complex and dissolve the aluminum chloride therein;
    C. filtering the reaction medium and collecting dimethyldichlorothianthrene as a solid.